(12) United States Patent (10) Patent No.: US 9,055,988 B2
Galgut et al. (45) Date of Patent: Jun. 16, 2015

(54) DENTAL IMPLANT ADAPTOR

(75) Inventors: Dana Galgut, Centurion (ZA);
Giuseppe Geldenhuys, Centurion (ZA);
Graham Alan Blackbeard, Centurion (ZA)

(73) Assignee: SOUTHERN IMPLANTS (PTY) LTD., Irene, Centurion (ZA)

(*) Notice: Subject to any disclaimer, the term of this patent is extended or adjusted under 35 U.S.C. 154(b) by 761 days.

(21) Appl. No.: 12/734,527

(22) PCT Filed: Nov. 7, 2008

(86) PCT No.: PCT/IB2008/054668
§ 371 (c)(1),
(2), (4) Date: Apr. 7, 2011

(87) PCT Pub. No.: WO2009/060415
PCT Pub. Date: May 14, 2009

(65) Prior Publication Data
US 2011/0183290 A1 Jul. 28, 2011

(30) Foreign Application Priority Data

Nov. 9, 2007 (ZA) .................................. 2007/09679
May 22, 2008 (ZA) .................................. 2008/04439

(51) Int. Cl.
*A61C 8/00* (2006.01)
*A61C 9/00* (2006.01)

(52) U.S. Cl.
CPC .............. *A61C 8/005* (2013.01); *A61C 8/0001* (2013.01); *A61C 8/006* (2013.01); *A61C 8/0066* (2013.01); *A61C 8/0068* (2013.01); *A61C 9/0053* (2013.01); *A61C 2008/0084* (2013.01)

(58) Field of Classification Search
CPC ...... A61C 8/005; A61C 8/006; A61C 8/0066; A61C 9/0053; A61C 8/00

USPC .................................................. 433/172–179
See application file for complete search history.

(56) References Cited

U.S. PATENT DOCUMENTS 4,758,161 A 7/1988 Niznick
4,975,059 A 12/1990 Sendax
(Continued)

FOREIGN PATENT DOCUMENTS

EP 1 310 217 A2 5/2003
WO WO 2004/002359 A1 1/2004
(Continued)

OTHER PUBLICATIONS

Nobel Biocare—2007—"Procedures & Products—Curvy Esthetic Abutment"—http://files.nobelbiocare.com/manuals/pdf/q307/20423_CurvyAbMan_EN.pdf.*

*Primary Examiner* — Cris L Rodriguez
*Assistant Examiner* — Mirayda A Aponte
(74) *Attorney, Agent, or Firm* — Marshall & Melhorn, LLC (57) ABSTRACT

A dental implant adaptor which is particularly suitable for dental crown implantation using a screw-retained protocol has a hollow body that can be mounted on a dental implant. The body includes a crown-receiving portion on which a dental crown can be mounted. The portion has a distal end and a proximal end and includes a first anti-rotation formation to prevent rotation between the adaptor and the crown. The body also has a laterally projecting collar at the proximal end of the crown-receiving portion which, in use, locates on the implant. There is also a second anti-rotation formation shaped for non-rotational engagement with the implant. The crown-receiving portion and collar together have an overall axial length in the range 3.5 mm to 7 mm and the collar has an axial thickness of 1.5 mm or less. Another described is an implant assembly incorporating the adaptor.

2 Claims, 9 Drawing Sheets

(56) References Cited

U.S. PATENT DOCUMENTS

| | | | |
|---|---|---|---|
| 5,564,924 A | 10/1996 | Kwan | |
| 5,733,124 A | 3/1998 | Kwan | |
| 5,782,918 A * | 7/1998 | Klardie et al. | 606/60 |
| 5,823,776 A * | 10/1998 | Duerr et al. | 433/173 |
| 7,014,464 B2 * | 3/2006 | Niznick | 433/173 |
| 7,108,510 B2 * | 9/2006 | Niznick | 433/173 |
| 7,291,013 B2 | 11/2007 | Aravena et al. | |
| 7,491,058 B2 | 2/2009 | Jorneus et al. | |
| 2006/0019219 A1 | 1/2006 | Saliger et al. | |
| 2006/0228672 A1 | 10/2006 | Hurson | |
| 2006/0263747 A1 | 11/2006 | Hurson | |
| 2007/0037123 A1 * | 2/2007 | Mansueto et al. | 433/173 |
| 2007/0059666 A1 * | 3/2007 | Zickman et al. | 433/173 |
| 2007/0072149 A1 * | 3/2007 | Rompen et al. | 433/173 |
| 2008/0057476 A1 * | 3/2008 | Zettler et al. | 433/173 |
| 2008/0085492 A1 * | 4/2008 | Hurson | 433/173 |
| 2009/0142732 A1 | 6/2009 | Kahdemann et al. | |
| 2011/0123948 A1 * | 5/2011 | Hinrichsen | 433/173 |
| 2012/0003609 A1 * | 1/2012 | Hung | 433/174 |

FOREIGN PATENT DOCUMENTS

| | | | |
|---|---|---|---|
| WO | WO 2004002358 A1 * | 1/2004 | |
| WO | WO 2006/101957 A1 | 9/2006 | |
| WO | WO 2007/025784 A2 | 3/2007 | |

* cited by examiner

DENTAL IMPLANT ADAPTOR

BACKGROUND TO THE INVENTION

THIS invention relates to a dental implant adaptor.

A conventional dental implant assembly consists of an implant, an abutment and a crown. The implant has a threaded shank which is screwed into the bone, the abutment is then fastened to the implant and the crown, which has the appearance of the original tooth and which is visible in the mouth after implantation, is fastened to the abutment.

While the implant and abutment may have standard designs, the crown must be individually manufactured in a dental laboratory. In modern practice a digital camera is placed in the patient's mouth or over a model thereof and optical scanning is used to register the position and shape of the implant and abutment, and the corresponding part of the crown is shaped according to the scanned data.

The shapes of the current implant/abutment components are however not ideal for optical scanning in situations where a "screw retained" protocol, in which the crown is held in position by a screw, is used. Where a "closed crown cemented" protocol is used, the relevant components are more suited to optical scanning but the protocol is not universally popular. This is because it is difficult to retrieve the crown in the event of, for instance, excess wear or fracture. Also, the protocol leads to formation of a cement junction line just beneath the soft tissue of the gum and this line can be visible and unsightly if soft tissue recession takes place.

SUMMARY OF THE INVENTION

According to one aspect of the present invention there is provided a dental implant adaptor comprising a hollow body mountable on a dental implant and including:

a crown-receiving portion on which a dental crown is mountable, the crown-receiving portion having a distal end and a proximal end and including a first anti-rotation formation to prevent rotation between the adaptor and a dental crown mounted on the crown-receiving portion, a laterally projecting collar at the proximal end of the crown-receiving portion, and a second anti-rotation formation shaped for non-rotational engagement with a dental implant, the crown-receiving portion and collar together having an overall axial length in the range 3.5 mm to 7 mm and the collar having an axial thickness of 1.5 mm or less.

In the preferred embodiments, the crown-receiving portion is at least partially of tapered shape. The tapered part may for example be generally conical with a cone angle in the range 1.5° to 5°, preferably about 3°. Preferably also the axial thickness of the collar is in the range 0.2 mm to 0.7 mm, possibly of the order of 0.3 mm, and the overall axial length of the tapered portion and crown together is in the range 4 mm to 5 mm, typically 4.3 mm.

The stated dimensions and conicity render the adaptor suitable for scanning and for use in a screw-retained protocol.

According to another aspect of the invention there is provided a dental implant assembly comprising:

an implant having a proximal end which can be anchored in a bone, an opposite, distal end and a threaded passage in the implant, an implant adaptor as summarised above which is engagable non-rotatably on the distal end of the implant through non-rotational engagement between the second anti-rotation formation and the implant, and a screw designed to extend through the adaptor and to be screwed into the threaded passage in the implant, thereby to anchor on the implant a crown which is, in use, fixed non-rotatably on the crown-receiving portion of the adaptor through non-rotational engagement of the first anti-rotation formation and the crown.

Yet another aspect of the invention provides a dental implant apparatus comprising:

a dental implant assembly as summarised above, the crown-receiving portion of the dental implant adaptor including at least a part which is of tapered shape, and a scanning and locating insert made of plastics material and having a tapered distal end and a threaded proximal end, the insert being shaped for its proximal end to be screwed into the threaded passage in the implant with its distal end bearing on the adaptor, thereby to secure the adaptor to the implant for scanning of the adaptor and implant in the mouth of a patient.

A further aspect of the invention provides a method of installing a dental crown in a patient's mouth, the method comprising the steps of providing a dental implant assembly according to claim 19, anchoring the implant in a patient's jaw, temporarily locating the implant adaptor on the implant in the patient's mouth, obtaining a scan of the adaptor and its surroundings in the patients mouth, using the scan to manufacture a crown mountable non-rotatably on the crown-receiving portion of the adaptor, the crown including a passage therethrough for the screw;

fixing the crown non-rotatably on the crown-receiving portion of the adaptor, outside the patient's mouth, and locating the assembled crown and adaptor non-rotatably on the implant in the patient's mouth and anchoring them to the implant by passing the screw through the passage in the crown and screwing it into the threaded passage in the implant.

Other features of the dental implant adaptor, assembly, apparatus and method are set forth in the appended claims.

BRIEF DESCRIPTION OF THE DRAWINGS

The invention will now be described in more detail, by way of example only, with reference to the accompanying drawings in which.

DESCRIPTION OF THE ILLUSTRATED EMBODIMENTS

Figure 1:
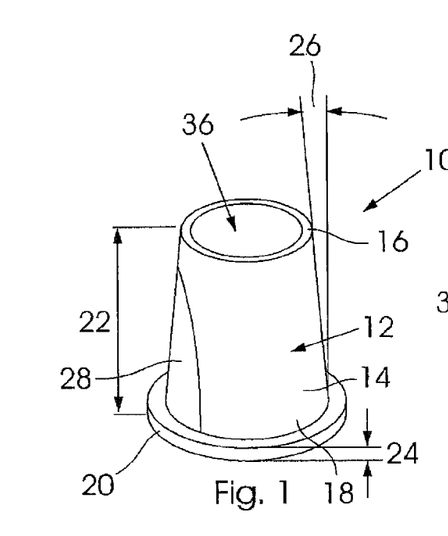
FIG. 1 shows a perspective view of a dental implant adaptor according to the invention.

FIG. 1 shows a first embodiment of dental implant adaptor 10 according to the invention. The view in this Figure is taken from the coronal end of the adaptor.

The adaptor 10 is made of a suitable non-corrosive and bio-compatible material, typically a suitable grade of titanium. The adaptor 10 includes a hollow body 12 including a generally conically tapered, crown-receiving or abutment portion 14 extending from a relatively narrow, distal or coronal end 16 to a relatively wide, opposite, proximal end 18. The hollow body 12 also includes a collar 20 which projects laterally at the relatively wide, proximal end. In general it is preferred that the overall axial length of the crown-receiving portion and collar together is in the range 3.5 mm to 7 mm, preferably 4 mm to 6 mm. The axial thickness of the collar is preferably 1.5 mm or less, most preferably in the range 0.2 mm to 0.7 mm. In this example the collar has an axial thickness of the order of 0.3 mm and the crown-receiving portion has an axial length of 4 mm, giving the crown-receiving portion and collar together an overall axial length of 4.3 mm. The cone or taper angle 26 is preferably in the range 1.5° to 5°, and in this example is 3°.

The numeral 28 indicates a first anti-rotation formation in the form of an outwardly extending, lateral protrusion or bulge on the external surface of the tapered crown-receiving portion 14. In the region of this protrusion the tapered crown-receiving portion 14 is non-circular in cross-section.

In other Figures of the drawings which illustrate dental implant adaptors according to the invention, features corresponding to those in FIG. 1 are designated by the same reference numerals.

Figure 2:
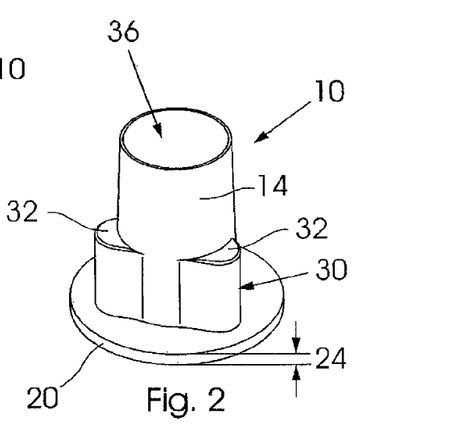
FIGS. 2 to 4 show perspective views of dental implant adaptors according other embodiments of the invention.

In the embodiment of FIG. 2, the crown-receiving portion 14 includes a conically tapered part 14.1 and a first anti-rotation formation 30 located between the tapered part and the collar 20. While the tapered part 14.1 has a circular cross-section throughout in this embodiment, the anti-rotation formation 30 has three equiangularly spaced apart projections in the form of lobes 32 defining a non-circular cross-sectional shape.

Figure 3:
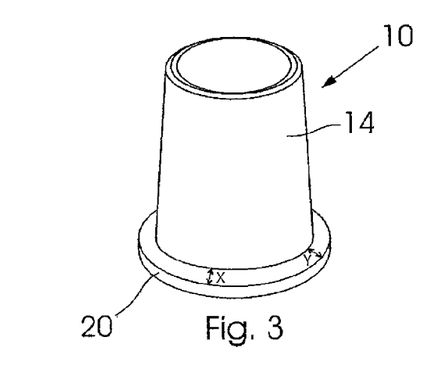

In FIG. 3, the crown-receiving portion 14 has a non-circular, elliptical cross-section throughout. This is demonstrated by the fact that, while the central axis of the crown-receiving portion coincides with that of the collar and the collar is circular in shape, the indicated dimensions x and y are different from one another. In this case the entire length of the crown-receiving portion between the distal end 16 and the collar at the proximal end serves as an anti-rotation formation.

Figure 4:
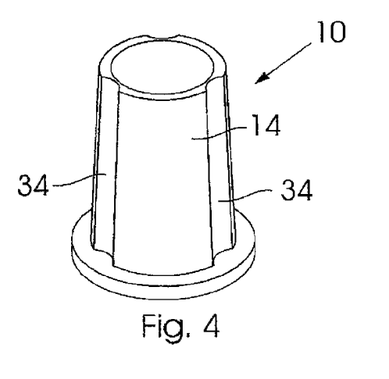

In FIG. 4, the crown-receiving portion 14 has anti-rotation formations in the form of channels or recesses 34 in its external, generally conical surface, giving it a non-circular cross-sectional shape throughout.

In FIGS. 13 to 37, the generally conical crown-receiving formation 14 includes an anti-rotation formation in the form of an outwardly extending protrusion or abutment 90. More is said below about the nature of the protrusion 90.

In each of FIGS. 1 to 4 and 13 to 37 the body 12 is hollow, the numeral 36 indicating the central hollow or bore of the body.

In use the anti-rotation formations, i.e. the bulge 28 in FIG. 1, the lobes 32 in FIG. 2, the elliptical cross-section in FIG. 3, the channels or recesses 34 in FIG. 4 and the protrusion 90 in FIGS. 13 to 37, serve to prevent relative rotation between a crown mounted on the crown-receiving portion 14 and the adaptor 10 when these components are fixed to one another as described in more detail below.

Figure 5:
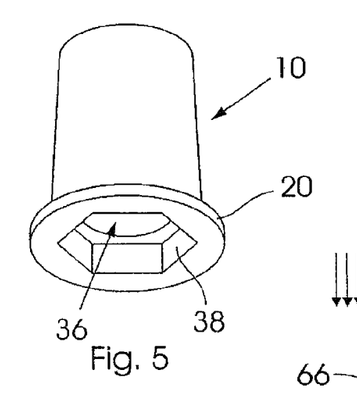
FIG. 5 shows a perspective view from the opposite end of an implant adaptor as shown in FIGS. 1 to 4.

The dental implant adaptor 10 includes a second anti-rotation formation, at its proximal end, to prevent rotation between the adaptor and a dental implant on which the adaptor is mounted in use, as described below. Referring by way of example to FIG. 5, which shows a perspective view of the adaptor 10 of FIG. 1 taken from the proximal end, the second anti-rotation formation 38 includes a socket of non-round, in this case hexagonal, shape. Referring also to FIG. 6, again by way of example, the anti-rotation formation 38 extends axially from the collar in a direction opposite to the crown-receiving portion 14. The formation 38 in this case includes a part 40, adjacent the collar 20, which has three equi-angularly spaced lobes 42 defining a non-circular cross-sectional shape and a hollow, round cylindrical part 44 arranged coaxially with the portion 14.

Figure 6:
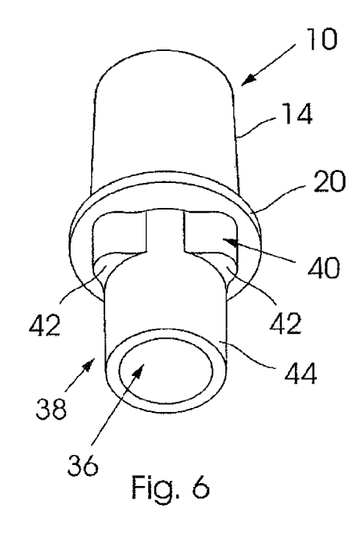
FIG. 6 shows a perspective view from the opposite end of another embodiment of dental implant adaptor.
Figure 22:
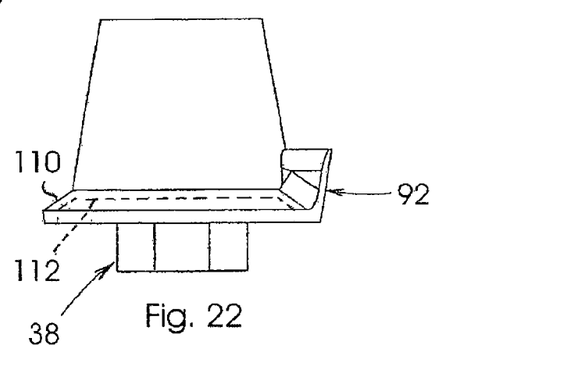
FIG. 22 shows a side view of the dental implant adaptor seen in FIG. 21.
Figure 23:
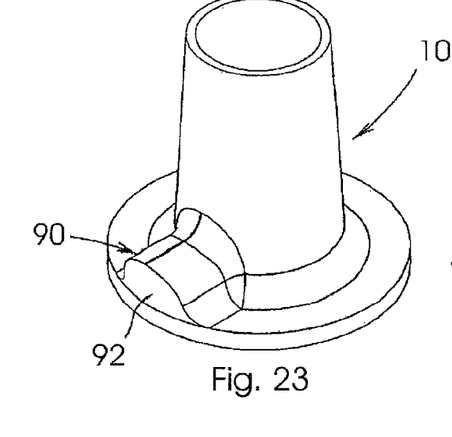
FIG. 23 shows a perspective view of a further embodiment of dental implant adaptor according to the invention.
Figure 24:
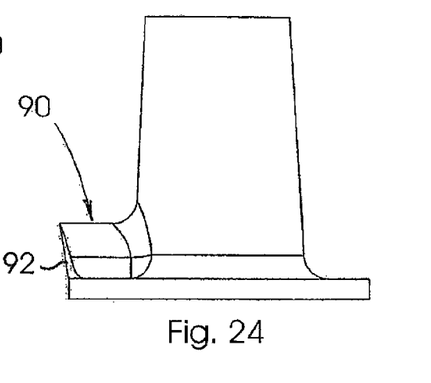
FIG. 24 shows a side view of the dental implant adaptor seen in FIG. 23.
Figure 25:
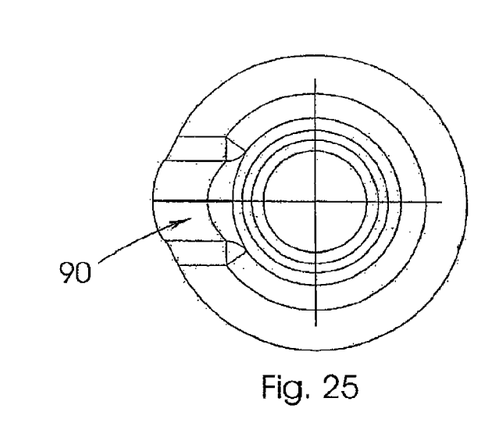
FIG. 25 shows a plan view of the dental implant adaptor seen in FIG. 23.
Figure 26:
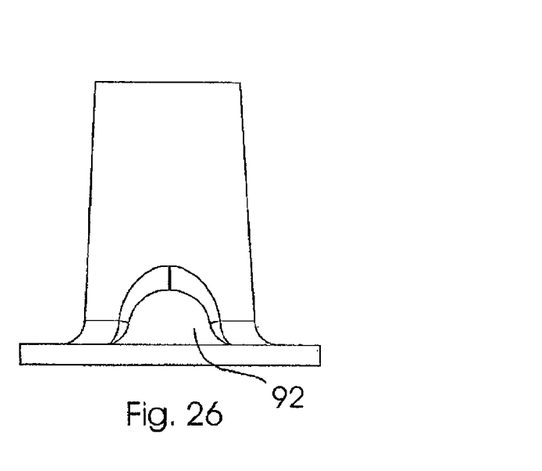
FIG. 26 shows another side view of the dental implant adaptor seen in FIG. 23.
Figure 27:
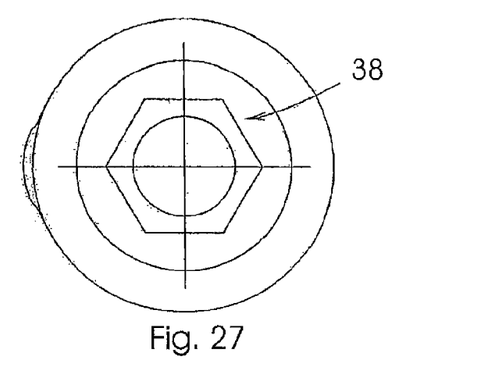
FIG. 27 shows a bottom view of the dental implant adaptor seen in FIG. 23.
Figure 33:
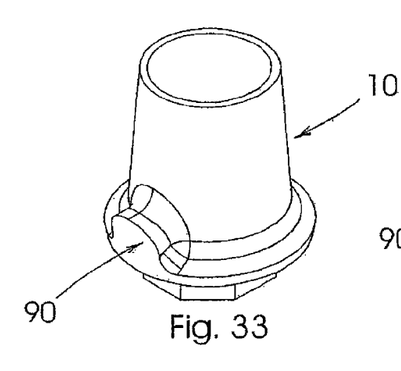
FIG. 33 shows a perspective view of a further embodiment of dental implant adaptor according to the invention.
Figure 34:
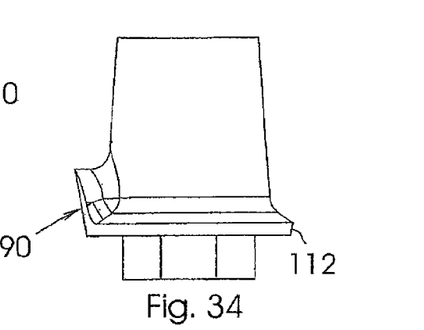
FIG. 34 shows a side view of the dental implant adaptor seen in FIG. 33.

From the descriptions of various embodiments of dental implant adaptor which follow in this specification, it will be understood that either one of the anti-rotation formations 38 such as those seen in FIGS. 5 and 6, or any other suitable type of anti-rotation formation, for example the formation 38 seen in FIG. 22 or FIGS. 33 and 34, can be provided on any of the described adaptors. So, for example, the adaptors seen in FIGS. 2 to 4 could include formations 38 as seen in FIG. 6 or FIGS. 22, 33 and 34 or the formation 38 seen in FIG. 6 could be replaced by a formation 38 as seen in FIG. 5 or as seen, in FIGS. 22, 33 and 34, and so on. In each case, the selection of the appropriate type of anti-rotation formation will be dictated by the particular implant which is used.

FIGS. 7 to 11 illustrate components of a dental implant assembly which includes a dental implant adaptor 10 of the type described above with reference to FIGS. 2 and 6. The assembly also includes an implant 50 which has a tapered, threaded shank 52 extending to a narrow, proximal end, a multi-lobed socket 54 complemental in shape to the formation 38 of the implant adaptor 10, a threaded passage 56 extending axially into the shank from the base of the socket 54 and a distal or coronal end 58.

The assembly further includes a crown 60, about which more is said below, and a prosthetic retaining screw 62.

In the implantation procedure, a hole is formed by drilling, reaming or other suitable procedure in a jaw bone 64 of the patient and the threaded shank 52 of the implant 50 is screwed into the hole such that the end of the implant is accessible above the bone. The implant may then be left, after closing up the wound site, for a period of time suitable for integration and stabilisation of the implant to take place. During healing of the soft tissue surrounding the implant site, a temporary abutment may be engaged with the coronal implant. After implant integration and stabilisation and removal of the temporary abutment, the implant adaptor 10 is located on the coronal end of the implant, as shown in FIG. 7, with the multi-lobed formation 38 of the adaptor received complementally and non-rotationally in the socket 54 of the implant.

Figure 7:
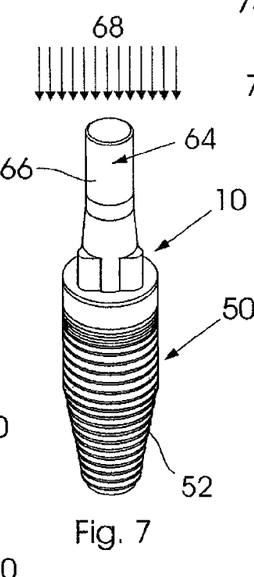
FIG. 7 illustrates a step in a dental implantation method.
Figure 12:
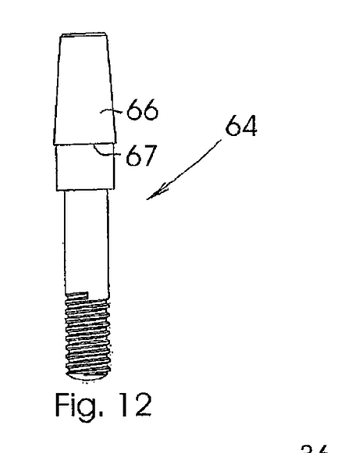
FIG. 12 shows a side view of a scanning and locating insert.

Next the shank of a plastic scanning and locating insert or pin 64 is passed through the central bore 36 of the adaptor 10 and is screwed into the threaded passage 56 of the implant 50, as shown in FIG. 7. As shown in FIG. 12, the insert 64 has a tapered head 66 terminating at a shoulder 67. When the insert is installed in the manner seen in FIG. 7, the shoulder 67 of the insert bears on the coronal end 16 of the adaptor 10 with the result that the insert holds the adaptor in place on the implant 50.

The head 66 of the insert 64 has a conical taper matching that of the tapered part 14.1 of the crown-receiving portion 14 of the abutment 10. Thus, when the insert has been screwed into position, the head 66 effectively forms a conical extension of the part 14.1, as shown in FIG. 7.

In the next step, a camera is inserted into the patient's mouth and is used to conduct a scan of the components described above and of the surrounding teeth, as indicated by the arrows 68 in FIG. 7. After completion of the scan, the insert 64 is unscrewed and the adaptor 10 is detached from the implant 50 and is removed from the patient's mouth. Prior to scanning a suitable contrast spray may be applied to the assembly of adaptor 10 and insert 64.

In the scan which is conducted, the insert 64 holds the adaptor 10 in position and provides an accurate indication of the position, shape and size of the adaptor 10 and passage 36.

Where the scanning camera is of a type providing simply a two-dimensional, axial image of the components, as indicated by the arrows 68 in FIG. 7, the tapered shapes of the part 14.1 of the crown-receiving portion 14 of the adaptor and of the head 66 of the insert 64 provide depth perception in the image.

The image captured by the camera is used in the manufacture of the crown 60, typically of ceramic. In some cases other information such as physical bite impressions of the patient's mouth may also be obtained to assist in accurate manufacture of the crown.

In the preferred technique, the camera captures one or more digital images which are fed to a computer controlled manufacturing apparatus, typically including a CNC milling machine, programmed to manufacture the crown from the input information.

The head 66 of the insert 64 has a length corresponding to the height of the crown which is to be manufactured. If necessary, the head 66 may be cut down as necessary to suit the crown height before scanning takes place.

Figure 8:
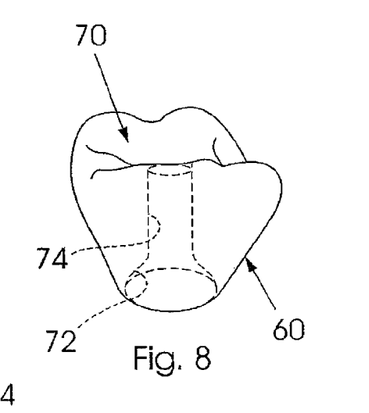
FIG. 8 shows a perspective view of a crown used in a dental implant assembly according to the invention.

As indicated above, the tapered shapes of the part 14.1 of the portion 14 of the adaptor 10 allow for depth perception even in a two-dimensional, axial scanning mode. This facilitates the formation of an axial passage 74 through the crown, as shown in FIG. 8, during crown manufacture. The axial passage 74 which is formed is complemental in shape to the portion 14 of the abutment 10 and includes a socket 72, adjacent the proximal end of the crown, which is complemental in shape to the anti-rotation formation 30, and extends to the occlusal or coronal end 70 of the crown. The manufactured crown is accordingly shaped for proper conformity and location in the mouth and for complemental location on the abutment 10.

The manufactured crown is then fixed to the implant adaptor 10 by cementing the portion 14 of the adaptor in the axial passage in the crown, thereby creating a unitary assembly consisting of the crown and adaptor. A suitable cement may, for instance, be Panavia™ or similar. Prior to cementing, the crown and portion 14 may be etched to improve cementation and Silane™ or a suitable porcelain activator may be applied to the portion 14.

These procedures are carried out outside the patient's mouth. The cooperation between the socket 72 and the anti-rotation formation 32, together with the cement, prevents rotation between the crown and adaptor.

Figure 9:
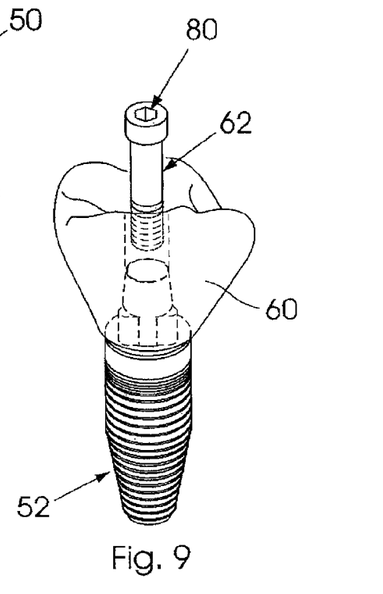
FIG. 9 shows a perspective view of a dental implant assembly according to the invention.
Figure 10:
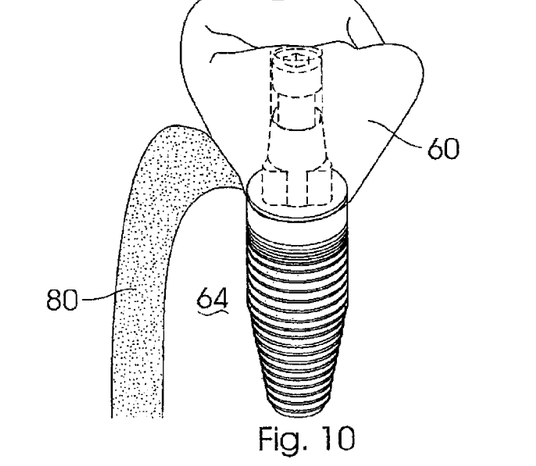
FIG. 10 shows a perspective view of the dental implant assembly of FIG. 9, after implantation.
Figure 11:
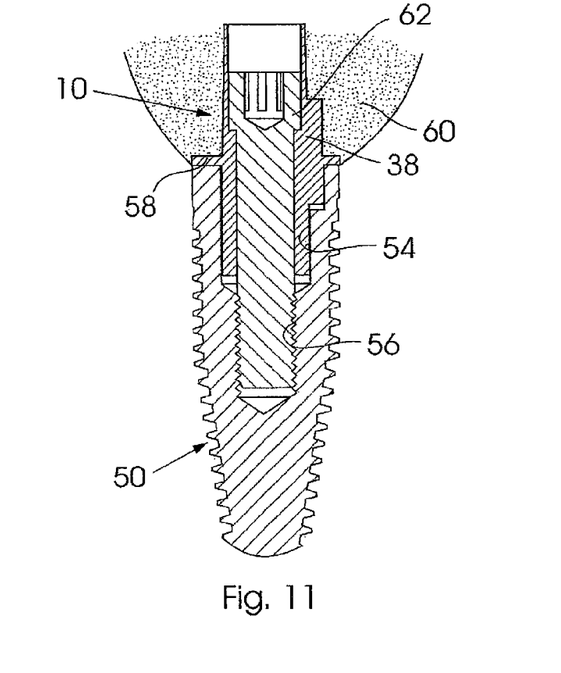
FIG. 11 shows a cross-sectional view of the implant assembly of FIG. 9.

The assembly of crown and adaptor is then taken to the patient's mouth and the adaptor 10 is mounted on the implant 50 with the collar 20 resting on the end of the implant and the multi-lobed formation 38 locating non-rotatably in the socket 54 of the implant. The shank of the retaining screw 62 is passed through the screw-receiving passage in the crown and through the bore 36 of the adaptor 10 as shown in FIGS. 9 to 11, and the threaded end of the shank is screwed into the passage 56 in the implant with a predetermined torque. The head of the screw bears on an internal shoulder 100 in the adaptor (see, for example, FIG. 17) and fastens the adaptor, and hence the crown, relative to the implant.

In practice, where the end of the tapered passage 74 is too narrow to allow the head of the screw 62 to pass through, the screw will be inserted through the passage 36, so that its head locates on the shoulder 100, before the crown is cemented in place. The passage 74 will then provide access to the screw head, by means of a narrow screw-driver or other tool, for the purposes of fastening the screw to the implant.

To facilitate the screwing operation the head of the screw has a socket formation 80 which has a hexagonal cross-section and which can be engaged by the appropriate tool. In other embodiments, the head of the screw may have a different tool-engaging formation, for example a slot or so-called "torx" or "unigrip" socket formation.

Figure 13:
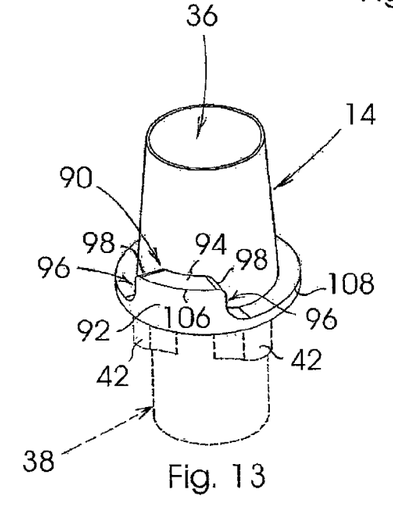
FIG. 13 shows a perspective view of another embodiment of dental implant adaptor according to the invention.
Figure 38:
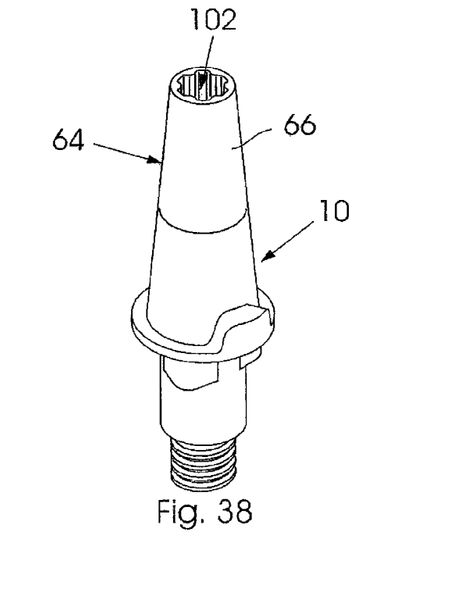
FIG. 38 shows a perspective view of an assembled insert and dental implant adaptor.

FIG. 38 illustrates an assembly of insert 64 and adaptor 10, in this case an adaptor 10 of the kind seen in FIG. 13, in which the insert is formed with a socket 102. This socket can be engaged by a suitable tool for the purposes of screwing the insert 64 to the implant prior to scanning. In FIG. 38 the socket is designed as a "unigrip" socket but it will be understood that the socket could have other designs, for example a hexagonal or "torx" design. Whereas the insert 64 seen in FIG. 7 is designed to be screwed in by hand, inserts such as that seen in FIG. 38 can be screwed in using a suitable spanner or other tool. This may be particularly advantageous in cases in which the implantation is carried out at the back of the mouth and manual access is difficult.

In practice, the socket 102 on the insert will usually match the socket on the screw 62, so the same tool can be used to screw both the insert and the screw 62.

The formation 38 of FIG. 6 type has three lobes 42 and from the above description persons skilled in the art will recognise that implant adaptors 10 employing this type of anti-rotation formation will be particularly suitable for use with so-called "tri-lobe internal connection" implants 50. As indicated above, adaptors 10 which employ different anti-rotation formations 38 will be suitable for use with other types of implant 50 where, in each case, the formation will engage complementarily and non-rotationally with the implant. For example, an implant adaptor of the type seen in FIG. 5 will be suitable for mounting on a so-called "external hex" implant, with the hexagonal mouth 38 of the bore in the adaptor serving as an anti-rotation formation that mates non-rotationally with the corresponding formation on the implant.

An advantage of dental implantation as described above is the fact that the screw-retained protocol allows the crown to be retrieved relatively easily for repair in the event of excessive wear or fracture. In comparison the conventional closed crown protocol makes crown retrieval extremely difficult and frequently results in destruction of the crown.

Referring again to FIGS. 13 and 14, the protrusion 90 has a cylindrical, radially outer surface 92 flush with the outer edge of the collar 20. The protrusion has an axial end surface 94 lying in a plane normal to the axis of the crown-receiving formation 14 and radially oriented circumferential end surfaces 96 which meet the end surface 94 at curved corners 98.

Figure 14:
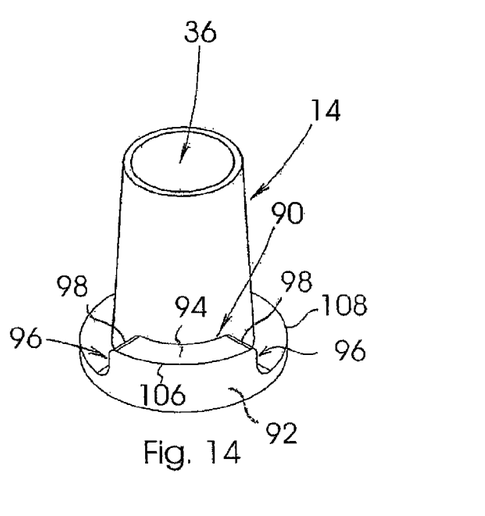
FIG. 14 shows a perspective view of a further embodiment of dental implant adaptor according to the invention.
Figure 15:
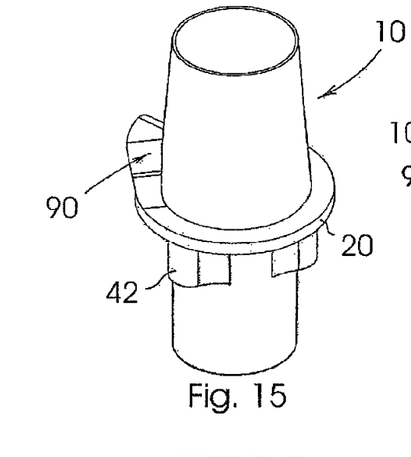
FIG. 15 shows a perspective view of a further embodiment of dental implant adaptor according to the invention.
Figure 16:
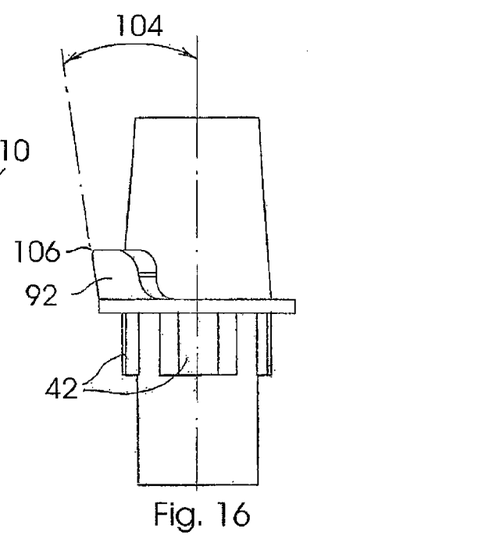
FIG. 16 shows a side view of the dental implant adaptor seen in FIG. 15.
Figure 17:
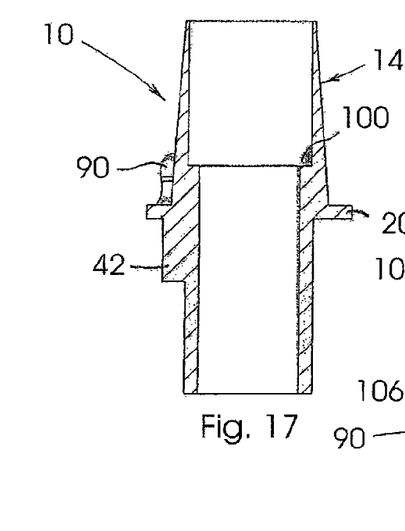
FIG. 17 shows a cross-section at the line 17-17 in FIG. 15.
Figure 18:
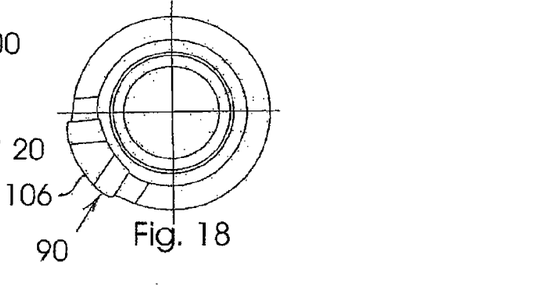
FIG. 18 shows a plan view of the dental implant adaptor seen in FIG. 15.
Figure 19:
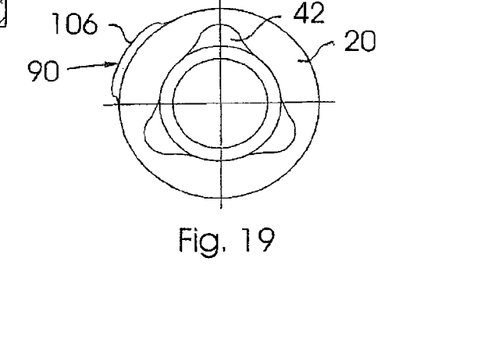
FIG. 19 shows a bottom view of the dental implant adaptor seen in FIG. 15.

The embodiment seen in FIGS. 15 to 19 differs from that of FIGS. 13 and 14 in that the outer surface 92 of the protrusion 90 is generally conical, not cylindrical. As is particularly clear from FIGS. 16, 18 and 19 the distal edge 106 of the protrusion projects radially beyond periphery of the collar 20. In a practical embodiment, the angle 104 is typically of the order of 10°.

As shown in FIG. 11 the crown may be manufactured so as to meet the collar at the edge 108 thereof on the side of the portion 14, and extends outwardly from that edge, completely encapsulating the portion 14 including the lobes 32. In the embodiments of FIGS. 13 and 14, the crown may again meet the collar at the edge 108, and may also meet the protrusion 90 at the edge 106. In this case the surface 92 of the protrusion is exposed. For this reason, the adaptor 10 will normally be oriented on the implant 50 such that the protrusion 90 faces in a palatal direction, i.e. into the mouth, and so will not be readily visible.

Referring to FIG. 13 it will be noted that the protrusion 90 is located at a circumferential position midway between two of the lobes 42 of the anti-rotation formation 38. With this feature it is possible to align the adaptor 10 on the implant 50 such that the third lobe 42 (not visible in FIG. 13) is oriented to the outside, i.e. opposite to the palatal direction, thereby ensuring that the protrusion 90 is palatally oriented. Thus the dental surgeon can orientate the adaptor 10 properly merely by facing the relevant lobe 42 to the outside.

It will be noted that the protrusion 90 in FIG. 14 has a greater circumferential extent than the corresponding protrusion 90 in FIG. 13. In FIG. 14 the protrusion extends circumferentially through an angle 100 of about 90° while in FIG. 13 the corresponding protrusion has a smaller circumferential extent.

Figure 20:
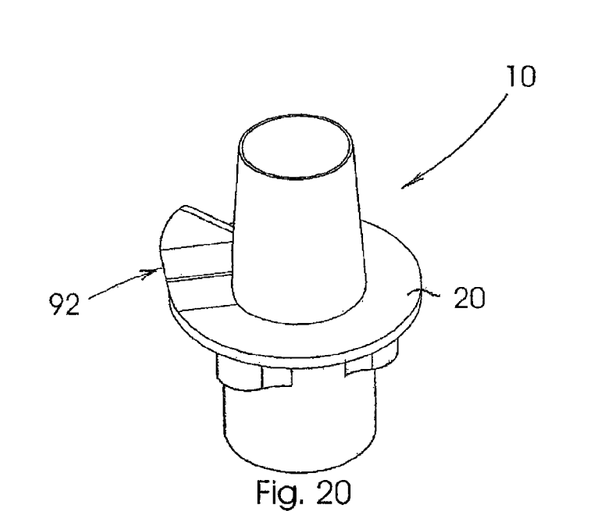
FIG. 20 shows a perspective view of a further embodiment of dental implant adaptor according to the invention.

The adaptor 10 seen in FIG. 20 differs from the adaptors described above in that the collar 20 has an increased radial dimension. In each case the radial size of the collar will be determined with reference to the implant 50 which is selected, the latter selection in turn inter alia depending on the size of the space available to receive the implant and crown.

Figure 21:
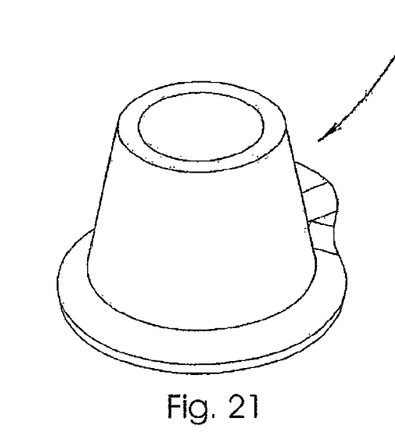
FIG. 21 shows a perspective view of a further embodiment of dental implant adaptor according to the invention.

The adaptor 10 seen in FIGS. 21 and 22 has an anti-rotation formation 38 which is hexagonal in cross-section and the collar has a conical outer surface 110. The inner surface 112 of the collar is shaped to mate with a conical surface on the implant 50. As in FIGS. 15 to 19, the surface 92 of the protrusion 90 is conical in shape.

In the adaptor 10 seen in FIGS. 23 to 27, the protrusion 90 has a somewhat more rounded shape than, for instance, the protrusions 90 seen in FIGS. 13, 14 and 15 to 19. Once again, the outer surface 92 of the protrusion has a generally conical shape. As illustrated the adaptor has an anti-rotation formation 38 including a hexagonal section socket but, as explained previously, this could in appropriate cases be replaced by a projecting anti-rotation formation generally of FIG. 6 type or of the type seen in FIGS. 21 and 22.

The adaptor 10 seen in FIGS. 28 and 29 again has a protrusion 90 with a somewhat rounded shape and a conical outer surface. However in this case, the collar 20 includes an outwardly flaring portion 20.1 and the portion 14 has an outwardly curved, transitional end region 14.2 extending to the edge 106 of the collar.

Figure 28:
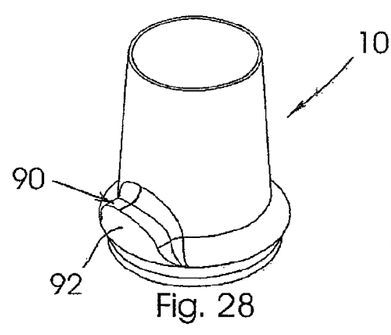
FIG. 28 shows a perspective view of a further embodiment of dental implant adaptor according to the invention.
Figure 29:
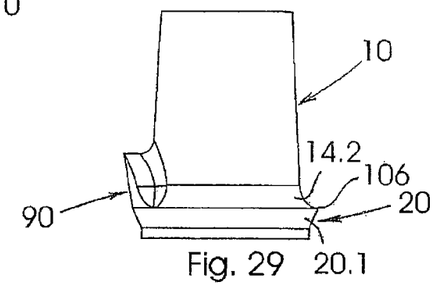
FIG. 29 shows a side view of the dental implant adaptor seen in FIG. 28.
Figure 30:
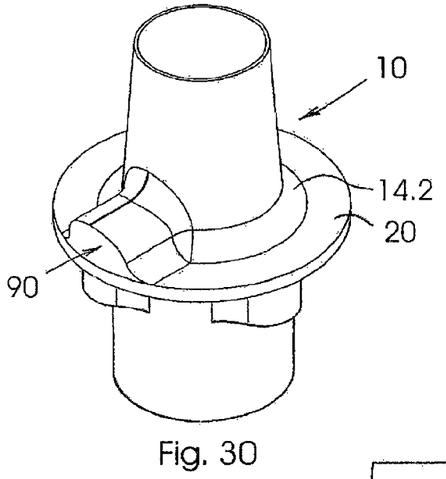
FIG. 30 shows a perspective view of a further embodiment of dental implant adaptor according to the invention.

FIG. 30 shows an adaptor 10 with, again, a somewhat rounded protrusion 90, a collar 20 with a greater radial extent and a transitional end region 14.2 similar to that seen in FIGS. 28 and 29.

Figure 31:
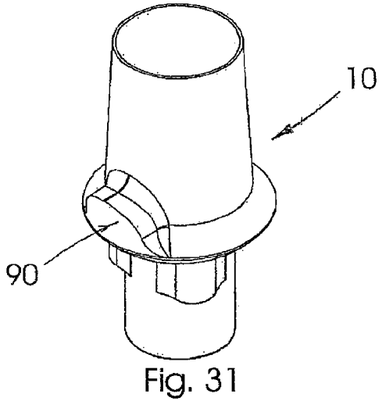
FIG. 31 shows a perspective view of a further embodiment of dental implant adaptor according to the invention.
Figure 32:
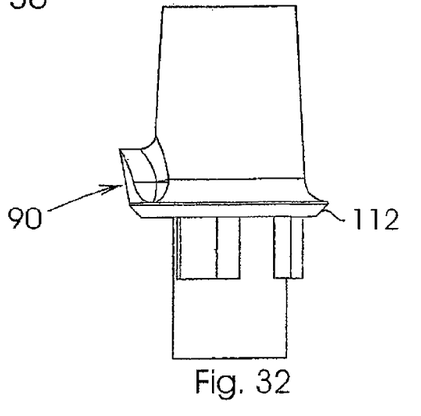
FIG. 32 shows a side view of the dental implant adaptor seen in FIG. 31.

FIGS. 31 and 32 show an embodiment in which the outer edge 112 of the collar 20 is markedly tapered. FIGS. 33 and 34 show an embodiment in which the corresponding taper is less pronounced and in which the anti-rotation formation 38 is, once again, provided as a hexagonal section projection.

Figure 35:
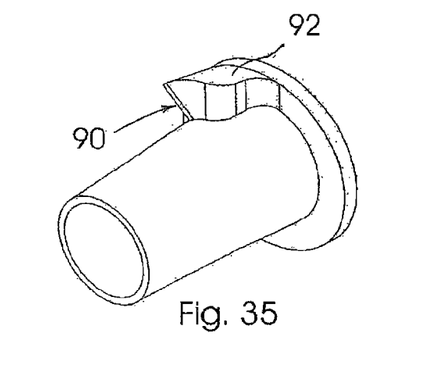
FIG. 35 shows a perspective view of a further embodiment of dental implant adaptor according to the invention.
Figure 36:
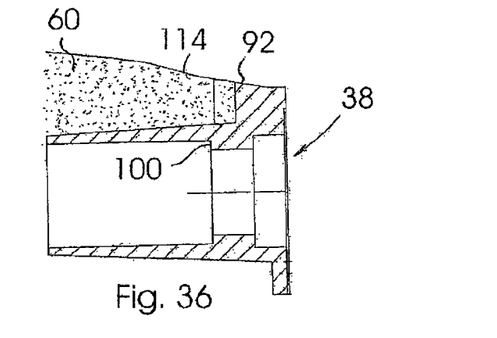
FIG. 36 shows a side view of the dental implant adaptor seen in FIG. 35.
Figure 37:
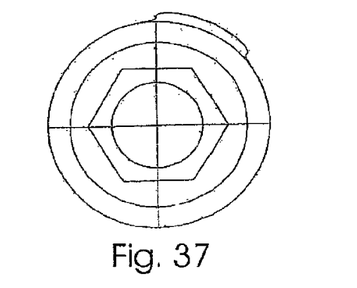
FIG. 37 shows a bottom view of the dental implant adaptor seen in FIG. 35.

FIGS. 35 to 37 show an embodiment, similar to that described with reference to FIG. 5, but in this case including a protrusion 90 somewhat similar to that of FIG. 13 and other embodiments described above. The anti-rotation formation 38 includes a hexagonal section socket.

The adaptor designs embodying the more rounded protrusion 90 are suitable for use with Lava™-type scanning and crown manufacturing systems where the crown is machined from the appropriate ceramic in a "green" state.

The protrusions 90 seen in FIGS. 13 to 37 are effective anti-rotation formations. Where the surfaces 96 are at right angles to any applied rotational force as, for example, in FIGS. 13, 14 and 15 to 19, such surfaces provide substantial resistance to any applied rotation forces. Also the fact that the protrusions extend to the periphery of the collar 20 means that they have a substantial radial extent to resist rotation.

It was mentioned above that the crown may meet the abutment at the edge 106 of the collar. However this may not always be so, since the exact shape of the crown in each case will be determined by the shape and size of the space available for implantation and desire for an aesthetic match with adjacent teeth. In some cases, the crown material may extend to the opposite edge of the collar. It has been found that those embodiments in which the surface 92 of the protrusion 90 is conically tapered can be particular advantageous in providing a smooth transition from the material of the adaptor to the crown material, as indicated by the crown surface 114 depicted diagrammatically in FIG. 34. The preferred taper angle of 10° has been found to suit a variety of crown shapes.

When compared to conventional practice, a major advantage of the invention as exemplified above is the fact that the crown is cemented to the adaptor outside the mouth. This means that it is possible, outside the mouth, to blend and polish the cement line 82 which is formed. In conventional practice in which the crown is cemented to the abutment inside the mouth, the cement line is typically below the soft tissue margin, making it difficult to blend and/or polish the line. Being very thin, i.e. 1.5 mm or less, preferably 0.2 mm to 0.7 mm, most preferably about 0.3 mm, the collar itself does not detract meaningfully from the desired aesthetics of the crown, even if the collar is not itself covered by crown material, i.e. is exposed.

The small thickness of the collar together with other, above-described dimensions for the adaptor 10, which are preferably present in all embodiments of the invention, make it possible for the cement line to be below the soft tissue margin and so unlikely to be exposed in an unsightly manner even if there is some tissue recession. In combination these factors lead to a dental implant which is aesthetically pleasing, particularly in the context of a screw-retained protocol which has the additional advantage of crown recovery if necessary.

The tapered shapes of the portion 14 and insert head 66 are particularly advantageous where two-dimensional scanning is used, because such shapes provide depth perception in the scanned images. In more sophisticated cases where scanning is carried out three-dimensionally, the tapered shapes may not be necessary.

The invention claimed is:

1. A method of installing a dental crown in a patient's mouth, the method comprising the steps of:
    providing a dental implant assembly, the dental impact assembly comprising:
        an implant having a proximal end which can be anchored in a bone, an opposite, distal end and a threaded passage in the implant,
        an implant adaptor, the dental impact adaptor comprising:
            a hollow body mountable on a dental implant, the body including:
                a crown-receiving portion on which a dental crown can be cemented, the crown-receiving portion having a central axis, a distal end and a proximal end and being of conically tapered shape from the proximal end to the distal end,
                a first anti-rotation formation to prevent rotation between the adaptor and a dental crown cemented on the crown-receiving portion, wherein the first anti-rotation formation extends circumferentially for no more than 90° about the central axis,
                a laterally projecting collar at the proximal end of the crown-receiving portion, and
                a second anti-rotation formation shaped and positioned to make direct non-rotational engagement with a dental implant,
            the crown-receiving portion and collar together having an overall axial length in the range 3.5 mm to 7 mm and the collar having an axial thickness of 1.5 mm or less,
            wherein the first anti-rotation formation comprises a protrusion which extends radially outwardly from the proximal end of the crown-receiving portion and distally from the collar at one angular position around the proximal end of the crown-receiving portion, and in that the collar has a distally disposed edge which lies in a plane normal to the central axis of the crown-receiving portion around the remainder of the proximal end of the crown-receiving portion, whereby the protrusion can be oriented palatally when the adaptor is engaged with the dental implant;
        which is engagable non-rotatably on the implant, through direct non-rotational engagement between the second anti-rotation formation and the implant, with a proximal surface of the collar of the adaptor in abutment with the distal end of the implant, and
        a screw designed to extend through the adaptor and to be screwed into the threaded passage in the implant, thereby to anchor on the implant a crown which is, in use, fixed non-rotatably on the crown-receiving portion of the adaptor through non-rotational engagement of the first anti-rotation formation and the crown,
    anchoring the implant in a patient's jaw,
        temporarily locating the implant adaptor on the implant in the patient's mouth,
        obtaining a scan of the adaptor and its surroundings in the patient's mouth,
        using the scan to manufacture a crown mountable non-rotatably on the crown-receiving portion of the adaptor, the crown including a passage therethrough for the screw;
        with the implant adaptor removed from the implant, fixing the crown non-rotatably on the crown-receiving portion of the adaptor, outside the patient's mouth, and
        locating the assembled crown and adaptor non-rotatably on the implant in the patient's mouth and anchoring them directly to the implant by passing the screw through the passage in the crown and screwing it into the threaded passage in the implant.

2. The method according to claim 1, wherein a locating and scanning insert is in inserted temporarily through the adaptor into the implant passage in order to provide an indication, in the scan, of the required position of the passage through the crown.

* * * * *